(12) United States Patent
Nentwick et al.

(10) Patent No.: US 10,278,802 B2
(45) Date of Patent: May 7, 2019

(54) SELF-ADHERENT IMPLANTS AND METHODS OF PREPARATION

(71) Applicant: Covidien LP, Mansfield, MA (US)

(72) Inventors: Brian Nentwick, Greenfield Center, NY (US); Ahmad Robert Hadba, Fort Worth, TX (US)

(73) Assignee: Covidien LP, Mansfield, MA (US)

( * ) Notice: Subject to any disclaimer, the term of this patent is extended or adjusted under 35 U.S.C. 154(b) by 576 days.

(21) Appl. No.: 14/970,701

(22) Filed: Dec. 16, 2015

(65) Prior Publication Data

US 2016/0100927 A1   Apr. 14, 2016

Related U.S. Application Data

(62) Division of application No. 13/549,915, filed on Jul. 16, 2012, now Pat. No. 9,241,781, which is a division
(Continued)

(51) Int. Cl.
*A61F 2/00* (2006.01)
*B65D 81/24* (2006.01)
(Continued)

(52) U.S. Cl.
CPC ........ *A61F 2/0095* (2013.01); *A61B 17/0401* (2013.01); *A61F 2/0063* (2013.01); *A61F 2/0077* (2013.01); *B65D 81/245* (2013.01); *A61B 17/085* (2013.01); *A61F 2002/0072* (2013.01); *A61F 2002/30448* (2013.01); *A61F 2220/005* (2013.01)

(58) Field of Classification Search
CPC .......... A61F 13/00072; A61F 13/00076; A61F 13/0008; A61F 13/551; A61F 13/5513; A61F 13/55135; A61F 13/5514; A61F 13/55145; A61F 13/5516; A61F 13/55165; A61F 13/55175; A61F 13/5519; A61F 2013/55195; A61F 15/001; A61F 15/00–15/003
See application file for complete search history.

(56) References Cited

U.S. PATENT DOCUMENTS 3,568,635 A * 3/1971 Poitras ................. A61F 15/002
                                                           118/122
3,612,265 A   10/1971 Dickerson
(Continued)

FOREIGN PATENT DOCUMENTS

DE         3630635 A1    3/1988
JP         11076367      3/1999
(Continued)

OTHER PUBLICATIONS

European Search Report for EP 08253182.3-1219 date of completion is Jun. 4, 2009 (4 pages).
(Continued)

*Primary Examiner* — Shaun David

(57) ABSTRACT

Implants are described herein which contain an activated adhesive on at least a portion of the surface of the implant. A release sheet may be positioned over at least a portion of the adhesive. Packages which contain the implants and methods of preparing the implants are also described.

10 Claims, 5 Drawing Sheets

Related U.S. Application Data of application No. 12/182,189, filed on Jul. 30, 2008, now abandoned.

(60) Provisional application No. 60/999,079, filed on Oct. 16, 2007.

(51) Int. Cl.
*A61B 17/04* (2006.01)
*A61B 17/08* (2006.01)
*A61F 2/30* (2006.01)

(56) References Cited

U.S. PATENT DOCUMENTS

| | | | |
|---|---|---|---|
| 3,636,956 | A | 1/1972 | Schneider |
| 3,797,499 | A | 3/1974 | Schneider |
| 3,835,834 | A | 9/1974 | Brown et al. |
| 3,861,985 | A | 1/1975 | Parlagreco |
| 4,279,344 | A * | 7/1981 | Holloway, Jr. ............ A61L 2/26 229/123.1 |
| 4,394,904 | A | 7/1983 | Larimore |
| 4,447,482 | A * | 5/1984 | Heinzelman ......... A61B 17/085 156/540 |
| 4,590,089 | A * | 5/1986 | Cartmell ............ A61B 5/04026 417/2 |
| 4,655,221 | A | 4/1987 | Devereux |
| 5,114,421 | A | 5/1992 | Polak |
| 5,219,077 | A * | 6/1993 | Transue ................ A61F 2/0063 206/438 |
| 5,292,328 | A | 3/1994 | Hain et al. |
| 5,333,753 | A | 8/1994 | Etheredge |
| 5,341,815 | A | 8/1994 | Cofone et al. |
| 5,593,441 | A | 1/1997 | Lichtenstein et al. |
| 5,722,943 | A | 3/1998 | Sessions |
| 5,844,016 | A | 12/1998 | Sawhney et al. |
| 5,900,245 | A | 5/1999 | Sawhney et al. |
| 5,972,008 | A | 10/1999 | Kalinski et al. |
| 6,042,592 | A | 3/2000 | Schmitt |
| 6,090,116 | A | 7/2000 | D'Aversa et al. |
| 6,217,894 | B1 | 4/2001 | Sawhney et al. |
| 6,287,316 | B1 | 9/2001 | Agarwal et al. |
| 6,352,710 | B2 | 3/2002 | Sawhney et al. |
| 6,375,662 | B1 | 4/2002 | Schmitt |
| 6,410,044 | B1 | 6/2002 | Chudzik et al. |
| 6,531,147 | B2 | 3/2003 | Sawhney et al. |
| 6,540,764 | B1 | 4/2003 | Kieturakis et al. |
| 6,541,678 | B2 | 4/2003 | Klein |
| 6,547,467 | B2 | 4/2003 | Quintero |
| 6,605,294 | B2 | 8/2003 | Sawhney |
| 6,632,457 | B1 | 10/2003 | Sawhney |
| 6,638,284 | B1 | 10/2003 | Rousseau et al. |
| 6,689,803 | B2 | 2/2004 | Hunter |
| 6,736,823 | B2 | 5/2004 | Darois et al. |
| 6,736,854 | B2 | 5/2004 | Vadurro et al. |
| 6,755,867 | B2 | 6/2004 | Rousseau |
| 6,803,069 | B2 | 10/2004 | Patnaik et al. |
| 6,914,169 | B1 | 7/2005 | Oota et al. |
| 6,924,370 | B2 | 8/2005 | Chudzik et al. |
| 6,936,052 | B2 | 8/2005 | Gellman et al. |
| 6,939,364 | B1 | 9/2005 | Soltz et al. |
| 9,241,781 | B2 | 1/2016 | Nentwick et al. |
| 2001/0000728 | A1 | 5/2001 | Sawhney et al. |
| 2001/0046518 | A1 | 11/2001 | Sawhney |
| 2002/0045919 | A1 | 4/2002 | Johansson-Ruden et al. |
| 2002/0049503 | A1 | 4/2002 | Milbocker |
| 2002/0103542 | A1 | 8/2002 | Bilbo |
| 2002/0111652 | A1 | 8/2002 | Kieturakis et al. |
| 2002/0127266 | A1 | 9/2002 | Sawhney et al. |
| 2002/0185396 | A1 | 12/2002 | Mainwaring et al. |
| 2002/0195367 | A1 * | 12/2002 | Dotta ................ A61F 13/0203 206/440 |
| 2003/0009181 | A1 | 1/2003 | Gellman et al. |
| 2003/0031697 | A1 | 2/2003 | Chudzik et al. |
| 2003/0035786 | A1 | 2/2003 | Hendriks et al. |
| 2003/0045774 | A1 | 3/2003 | Staskin et al. |
| 2003/0074041 | A1 | 4/2003 | Parry et al. |
| 2003/0104032 | A1 | 6/2003 | Sawhney et al. |
| 2003/0146117 | A1 | 8/2003 | Raia et al. |
| 2003/0171823 | A1 | 9/2003 | Zotti et al. |
| 2003/0212461 | A1 | 11/2003 | Vadurro et al. |
| 2003/0212462 | A1 | 11/2003 | Gryska et al. |
| 2004/0009205 | A1 | 1/2004 | Sawhney |
| 2004/0019360 | A1 | 1/2004 | Farnsworth et al. |
| 2004/0033264 | A1 | 2/2004 | Sawhney |
| 2004/0146546 | A1 | 7/2004 | Gravett et al. |
| 2004/0181288 | A1 | 9/2004 | Darois et al. |
| 2004/0202625 | A1 | 10/2004 | Daniloff et al. |
| 2004/0215231 | A1 | 10/2004 | Fortune et al. |
| 2004/0234574 | A9 | 11/2004 | Sawhney et al. |
| 2005/0004599 | A1 | 1/2005 | McNally-Heintzelman et al. |
| 2005/0010078 | A1 | 1/2005 | Jamiolkowski et al. |
| 2005/0087456 | A1 * | 4/2005 | Oka ...................... A61J 1/2093 206/219 |
| 2005/0136091 | A1 | 6/2005 | Chudzik et al. |
| 2005/0153090 | A1 | 7/2005 | Marchitto et al. |
| 2005/0175665 | A1 | 8/2005 | Hunter et al. |
| 2006/0025785 | A1 | 2/2006 | Cully et al. |
| 2007/0027415 | A1 * | 2/2007 | Kopreski ................ A61F 7/106 602/2 |
| 2007/0170080 | A1 * | 7/2007 | Stopek ............ A61B 17/06114 206/438 |
| 2007/0250177 | A1 | 10/2007 | Bilbo |
| 2008/0077104 | A1 * | 3/2008 | Baer .................... A61F 13/551 604/385.13 |
| 2008/0131190 | A1 | 6/2008 | Goodman et al. |
| 2008/0172015 | A1 * | 7/2008 | Okada ................ A61F 13/0203 604/307 |
| 2008/0269710 | A1 * | 10/2008 | Caracci ............ A61F 13/55135 604/385.06 |
| 2012/0217176 | A1 * | 8/2012 | Dacey ................... A61F 2/0095 206/204 |

FOREIGN PATENT DOCUMENTS

| | | |
|---|---|---|
| WO | 9812243 A1 | 3/1998 |
| WO | 2005037136 A2 | 4/2005 |
| WO | 2007028046 A2 | 3/2007 |

OTHER PUBLICATIONS

European Search Report for EP 11191001.4-1219 date of completion is Jun. 26, 2012 (13 pages).

* cited by examiner

SELF-ADHERENT IMPLANTS AND METHODS OF PREPARATION

CROSS-REFERENCE TO RELATED APPLICATION

The present application is a divisional application of U.S. patent application Ser. No. 13/549,915, filed Jul. 16, 2012, which issued as U.S. Pat. No. 9,241,781 on Jan. 26, 2016, which is a divisional application of U.S. patent application Ser. No. 12/182,189, filed Jul. 30, 2008, now abandoned, which claims the benefit of and priority to U.S. Provisional Application No. 60/999,079 filed on Oct. 16, 2007, the disclosures of each of the above-identified applications are hereby incorporated by reference in their entirety.

BACKGROUND

Technical Field

The present disclosure relates to self-adherent medical implants and packaging for such implants. Methods of preparing self-adherent implants are also disclosed.

Background of Related Art

Currently methods for securing medical implants, e.g., surgical meshes, to tissue include the use of a variety of fasteners (such as tacks or staples) alone or in combination with adhesives.

To work properly fasteners may need to be driven into specific areas of the implant as well as specific areas of the target tissue. As a result, the application of fasteners typically requires the use of graspers or other equipment to manipulate the implants and ensure that the fastener is properly positioned relative to both the implant and the target tissue. Such manipulations, while necessary with conventional fasteners, may undesirably increase the duration of the surgical procedure. In addition, the fasteners support the implants only at the point of penetration and do not distribute the load across the entire surface of the implant.

Known methods of using adhesives to secure medical implants to target tissue normally require the implants to be contacted with the adhesive immediately prior to implantation, during the surgery. As a result, the surgeon normally handles implants coated with adhesive materials. These adhesive materials may interact with any surface with which the implant comes into contact, e.g., medical instruments, a surgeon's hands or gloves, tissue other than the intended target tissue, etc.

It would be advantageous to provide implants that do not require the use of a fastening device, and that reduce the likelihood that the adhesive-bearing implant will prematurely adhere to unintended surfaces the implant may encounter prior to implantation.

SUMMARY

Accordingly, the implants described herein contain an adhesive on at least a portion of the surface of the implant and a release sheet overlying at least a portion of the adhesive.

Packages for containing implants having an activated adhesive positioned on at least a portion of a surface of the implant are also described. The package includes an internal surface overlying at least a portion of the activated adhesive when the package is closed, wherein at least a portion of the internal surface is a release sheet.

In embodiments, the package includes a first cavity containing an adhesive, a second cavity positioned adjacent the first cavity and configured to contain an implant and a rupturable barrier positioned between the first and second cavity. Rupture of the rupturable barrier allows the adhesive to communicate with at least a portion of the second cavity or implant. Dispensers for activating such packaged implants are also contemplated by this disclosure. The dispensers include a compartment containing the above-described packaged implant. The compartment includes a dispensing opening for allowing the passage of the packaged implant therethrough and a structure for rupturing the rupturable barrier of the packaged implant Methods for preparing a self-adherent implant are also described. The methods include the steps of applying an activated adhesive on at least a portion of the implant and overlying at least a portion of the activated adhesive with a release sheet.

DETAILED DESCRIPTION OF PREFERRED EMBODIMENTS

Figure 1:
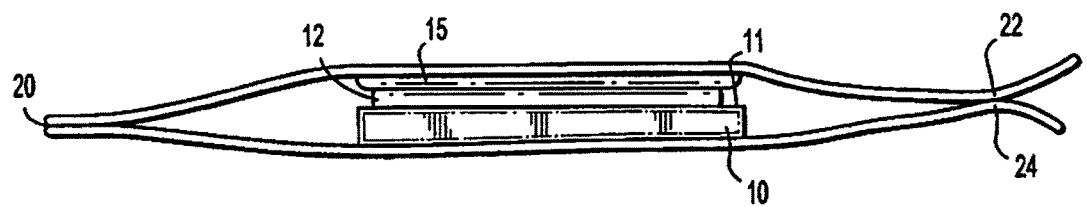
FIG. 1 shows a side view of a packaged implant in accordance with an illustrative embodiment described herein.

Medical implants that are self-adherent, packaging used to contain the implants, dispensers for activating the packaged implants and methods of preparing the self-adherent implants are all described herein. The implants contain an adhesive on at least a portion of the surface of the implant and a release sheet positioned over at least a portion of the adhesive.

As used herein, the term "implant" is used in the broadest sense and includes any biocompatible material that can be inserted into a body (human or any other animal) and which may remain in that body for at least some time. Some specific non-limiting examples of suitable implants include surgical meshes, patches, suture anchors, slings, grafts, bone plates, drug delivery devices, wound dressings, woven devices, non-woven devices, braided devices, adhesion barriers, tissue scaffolds, felts, pads, foams, films, fleeces, pledgets, buttresses, and other supportive medical devices. In some embodiments, the self-adherent implant is used to support tissue in pelvic floor prolapse, any type of hernia repair, cosmetic surgeries, arteriole bypass surgeries and wound closures. In embodiments, the implant is a surgical mesh.

The implants described herein can be formed from any sterilizable material that has suitable physical properties for the intended use of the implant. For example, the implants can be made from bioabsorbable, non-bioabsorbable, natural or synthetic polymeric materials, metallic materials and combinations thereof. Some specific non-limiting examples of suitable absorbable materials which may be utilized to form the implants include trimethylene carbonate, caprolactone, dioxanone, glycolic acid, lactic acid, glycolide, lactide, alkyl derivatives of trimethylene carbonate, delta.-valerolactone, β-butyrolactone, γ-butyrolactone, ε-decalactone, hydroxybutyrate, hydroxyvalerate, 1,4-dioxepan-2-one (including its dimer 1,5,8,12-tetraoxacyclotetradecane-7,14-dione), 1,5-dioxepan-2-one, 6,6-dimethyl-1,4-dioxan-2-one and polymer blends, homopolymers, copolymers and combinations thereof. Some specific non-limiting examples of suitable non-absorbable materials which may be utilized to form the medical implant include polyethylene, polypropylene, polyester, polyethylene terephthalate, polytetrafluoroethylene, polyaryletherketone, acrylic, polyamides, aramids, fluoropolymers, polybutester, silicone and flurocarbons cotton, linen, silk, polyamides, polyhexamethylene adipamide, polyhexamethylene sebacamide, polycapramide, polydodecanamide, and polyhexamethylene isophthalamide, polymer blends, homopolymers, copolymers and combinations thereof. In addition, the polymeric materials can include a naturally occurring biological molecule, or a variant thereof, such as collagen, gelatin, cellulose, starches, polysaccharides, alginate, chitosan, hyaluronic acid and combinations thereof. Also, some examples of metallic materials include, stainless steel, metal alloys, and shape-memory materials, e.g., nitinol.

The implants may contain any adhesive capable of adhering or attaching the implant to the target tissue. The adhesive may be biodegradable, non-biodegradable, bioabsorbable, non-bioabsorbable, natural, synthetic, and any combination thereof. The adhesives may include, for example, α-cyanoacrylates, isocyanates, polyurethanes, polyamines, polyamides, polymethacrylates, polyacrylates, and other synthetic monomers and polymers and combinations thereof. Some non-limiting examples of natural materials that may be positioned on at least a portion of the implant include fibrin, collagen, albumin, thrombin, gelatin, proteins and combinations thereof.

The adhesives may be activated at the time of application to the implant, or may require activation subsequent to application to the implant. By the term activated, it is meant that the adhesive is tacky without any further treatment and will adhere to surfaces with which it comes into contact. In embodiments, the adhesive is a material which is prepared to react with the target tissue to attach the implant without requiring activation or the addition of an initiator, diluent or cross-linker. That is not to say that initiators, diluents and cross-linkers may not be used, but rather that in the interest of efficiency, packaged implants which contain an activated adhesive are advantageous.

The adhesive can be positioned on any portion of the implant and in any manner suitable to coating an implant. In some embodiments, the adhesive is positioned on an outer surface of the implant. In some embodiments, the adhesive is allowed to penetrate into the implant. Some suitable methods for applying the adhesive to the medical device include, but are not limited to, dipping, brushing, spraying, painting, dotting, layering, patterning and wiping. In some embodiments, the adhesive may be applied by dip coating the medical implant directly into an adhesive solution. In other embodiments, the adhesive is in the form of a solid, e.g., powder, particulate matter or coating layer which may be sprayed, wiped or brushed onto the surface of the implants.

In embodiments in which the implant may be used to support tissue, certain portions of the implant may require more adhesive to fully support a given tissue. It is envisioned that the adhesive may be placed onto the medical implant in any pattern, and in varying concentrations, to further enhance the implant's ability to adhere to and support the target tissue.

A release sheet is positioned over at least a portion of the adhesive. The release sheet is designed to prevent contact or interaction with the adhesive prior to implantation thereby allowing medical personnel to handle the implant without fear of prematurely attaching the implant to an unintended surface. The release sheet also allows the implant to be folded, rolled or twisted in any manner while preventing the adhesive from contacting any portion of the implant thereby preventing the implant from sticking to itself. The release sheet may be made from any bioabsorbable or non-bioabsorbable material which is non-reactive to the adhesive. Some examples include, but are not limited to, polylactones, polytetrafluoroethylene, polyolefins, metalized polymer films, metallic foils and combinations thereof. In particularly useful embodiments, the release sheet may be made from polytetrafluoroethylene.

In some embodiments, the release sheet is made of a material which dissolves when placed in contact with water, saline or other natural bodily fluids including blood, mucous, sweat, saliva and the like. Some examples of dissolvable materials include, but are not limited to, polyvinyl pyrrolidones, polyethylene glycols, polyvinyl alcohols, polyacrylic acids, carboxymethylcellulose, alginates, hyaluronic acids, dextrans, polysaccharides, gelatins, and combinations thereof. The dissolvable release sheet is designed to prevent contact or interaction with the adhesive prior to implantation and expose the adhesive after interaction with a particular bodily fluid in which the release sheet is dissolvable.

Turning now to FIG. 1, implant 10 is shown containing an adhesive 12 positioned on at least a portion of the surface 11 of implant 10 and a release sheet 15 overlying at least a portion of adhesive 12 to inhibit contact of adhesive 12. Package 20, which includes top layer 22 and bottom layer 24, contains implant 10 including adhesive 12 and release sheet 15. It is envisioned that top layer 22 of package 20 may be opened or peeled away from bottom layer 24 to access implant 10 while adhesive 12 remains covered by release sheet 15. Implant 10 may then be positioned at the site of implantation by medical personnel while release sheet 15 remains in contact with adhesive 12. Medical personnel may then remove release sheet 15 from implant 10 to expose adhesive 12 and position the adhesive 12 directly into contact with the target tissue for a period of time sufficient for adhesive 12 to form a bond with the target tissue.

Figure 2:
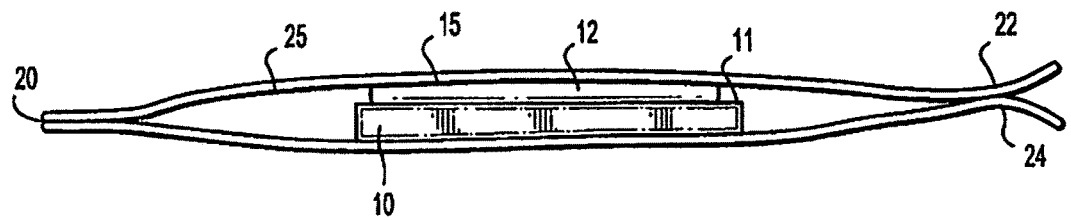
FIG. 2 shows a side view of a packaged implant in accordance with another illustrative embodiment described herein.

In other embodiments, as shown in FIG. 2, top layer 22 of package 20 includes an internal surface 25, a portion of which is release sheet 15. As described herein top layer 22 of package 20 may be opened or peeled away from bottom layer 24 to access implant 10 including adhesive 12. Top layer 22 includes a portion of which acts as a release sheet. The top layer may itself be made from a material that acts as a release sheet, or as shown in FIG. 2 top layer 22 may have release sheet 15 adhered thereto. Upon removal of bottom layer 24, top layer 22 will remain with implant 10 to protect against inadvertent contact with adhesive 12. Once implant 10 has been properly positioned, medical personnel may then remove top layer 22 (including release sheet 15) from implant 10 to expose adhesive 12 and position adhesive 12 directly into contact with the target tissue for a period of time sufficient for adhesive 12 to form a bond with the target tissue.

The package may be any conventional enclosure for storing implants. Some examples of useful packages include, but are not limited too, pouches, paper retainers, plastic retainers, bags, trays, envelopes, Tyvek® bags, foil-packs, and the like. It is envisioned that the packages may be sealable, non-sealable, breathable, non-breathable, peelable, resealable, and combinations thereof.

The package may be manufactured from any material known to those skilled in the art which is suitable for receiving or storing an implant. Some examples of suitable materials include, but are not limited to, polycarbonate, high-density polyethylene, polyethylene, polypropylene, thermoplastic elastomers, thermosets, thermoplastic resins, metalized polymers, poly(ethylene terephthalate), polytetrafluoroethylene, $\varepsilon$-caprolactone, glycolide, l-lactide, d,l-lactide, d-lactide, meso-lactide, trimethylene carbonate, 4,4-dimethyl-1,3-dioxan-2-one, p-dioxanone, dioxepanone, $\delta$-valerolactone, $\beta$-butyrolactone, $\varepsilon$-decalactone, 2,5-diketomorpholine, pivalolactone, $\alpha,\alpha$-diethylpropiolactone, 6,8-dioxabicyclooctan-7-one, ethylene carbonate, ethylene oxalate, 3-methyl-1,4-dioxane-2,5-dione, 3,3-dimethyl-1,4-dioxane-2,5-dione, polyolefins, polysiloxanes, polyalkylene glycols, polyacrylates, aminoalkyl acrylates, polyvinylalcohols, polyvinylpyrrolidones, polyoxyethylenes, polyacrylamides, poly(2-hydroxy-ethylmethacrylate), polymethacrylamide, dextran, alginic acid, sodium alginate, polysaccharides, gelatin and copolymers, homopolymers, and block copolymers thereof.

Figure 3A:
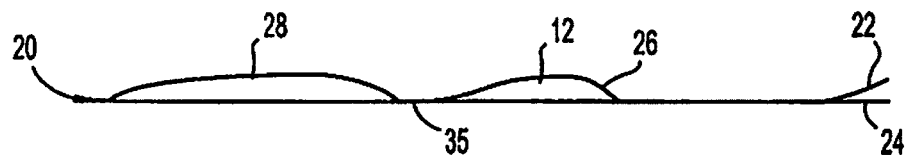
FIG. 3A shows a side view of a packaged implant in accordance with a two-compartment illustrative embodiment described herein.
Figure 3B:
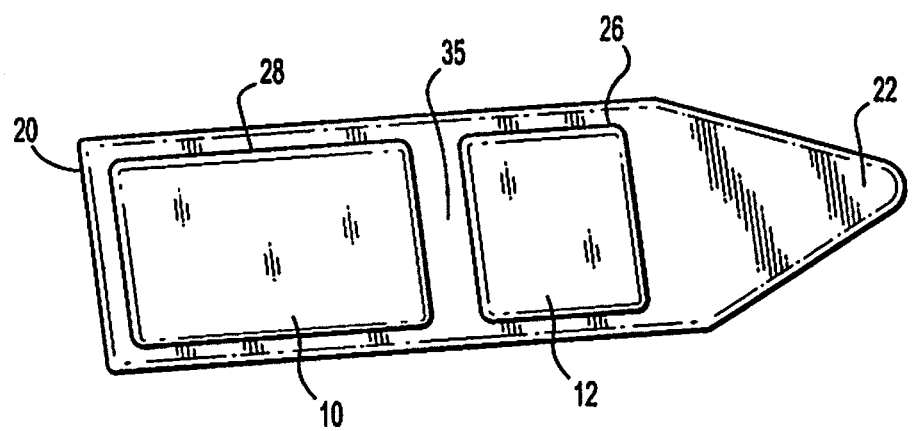
FIG. 3B shows a top view of the packaged implant of FIG. 3A.

The package is dimensioned and configured to receive an implant. In some embodiments, the package may include a single cavity for receiving the implant. In other embodiments, the package may include more than one cavity for receiving the implant and the adhesive separately. For example, as shown in FIGS. 3A and 3B, package 20 may include a first cavity 26 containing an adhesive 12 and a second cavity 28 positioned adjacent first cavity 26 and configured to contain implant 10. Package 20 further includes rupturable barrier 35 which is positioned between first cavity 26 and second cavity 28. Upon rupture of rupturable barrier 35, adhesive 12 can communicate with at least a portion of second cavity 28.

It is envisioned that prior to implantation, the barrier may be pierced, broken, removed or opened to allow the adhesive contained in the first cavity to flow onto at least a portion of the implant contained in the second cavity thereby positioning the adhesive on at least a portion of the implant. In embodiments, the barrier may be formed by a portion of the top and bottom layers of packaging. In other embodiments, the barrier may be a separate member positioned between the first and second cavity, which when exposed to a certain force, e.g., pressure, temperature, etc., the barrier will break or move to allow for the passage of the adhesive from the first cavity to the second cavity. As further shown in FIG. 3B, top layer 22 and bottom layer 24 of package 20 may be heat-sealed around the perimeter of package 20 and may be peeled apart to open package 20 to remove implant 10 having at least a portion of adhesive 10 positioned thereon.

Figure 4:
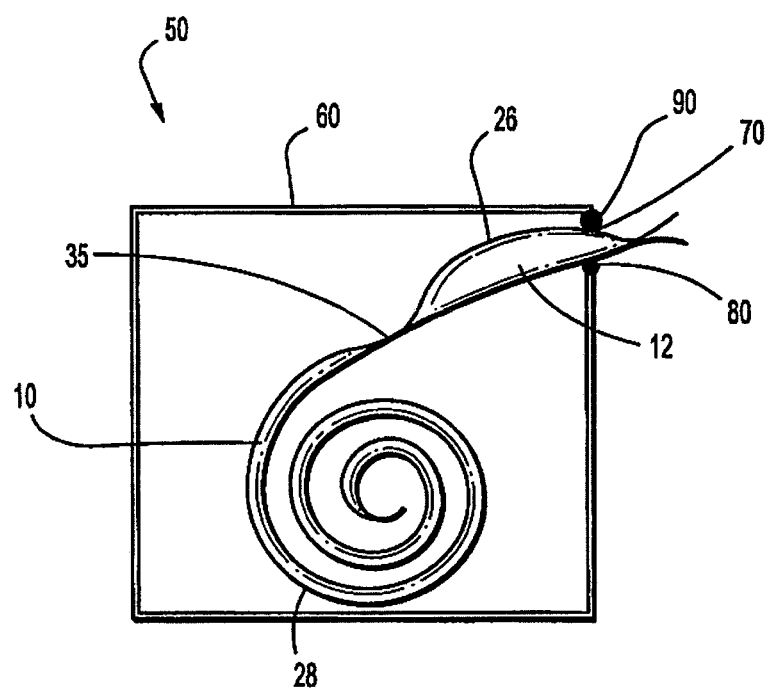
FIG. 4 shows a cross-sectional view of an illustrative embodiment of a dispenser for the packaged implant of FIG. 3A.

Turning now to FIG. 4, a dispenser 50 is shown including compartment 60 for containing package 20 of the type shown in FIG. 3A having first cavity 26 containing a medical adhesive 12, a second cavity 28 configured to contain a medical implant 10 and a rupturable barrier 35 therebetween. Compartment 60 further includes a dispensing opening 70 and a structure 80 for rupturing the rupturable barrier 35. Because compartment 26 is thicker than opening 70, pulling package 20 out of compartment 60 through opening 70 will result in rupture of rupturable barrier 35. Structure 80 in this embodiment is a contoured ridge that reduces the size of opening 70 and provides a smooth surface against which package 20 is compressed to rupture rupturable barrier 35 without tearing open compartment 36. In this manner, adhesive 12 can move into compartment 28 without leaving the interior of package 20. Thus, dispensing opening 70 is designed and configured to allow for the passage of the packaged implant out of compartment 60, but only after the rupturable barrier has been ruptured and at least some of adhesive 12 moves into cavity 28 and into contact with implant 10.

As package 20 is withdrawn from dispenser 50, structure 80 applies pressure, pierces or forces open rupturable barrier 35 thereby allowing adhesive 12 to flow from first cavity 26 to second cavity 28. Dispenser 50 may further include structure 90 for distributing the adhesive over at least a portion of implant 10. Examples of structures capable of distributing the adhesive to at least a portion of the implant include, but are not limited to, rollers, brushes, wipers and the like. In particularly useful embodiments, the dispenser will include at least one roller to assist in spreading the adhesive onto the implant as the package is withdrawn from the dispenser.

It is envisioned that following the removal of the packaged implant from the dispenser, the package may be opened to expose the coated implant. In some embodiments, the coated implant may remain in a portion of the package, typically the bottom portion of the package, so that the coated implant may be manipulated without prematurely attaching to an unintended surface.

Figure 6A:
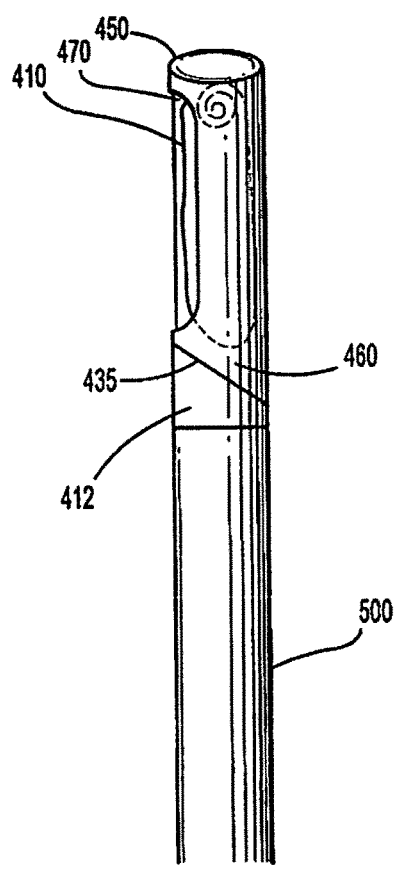
FIGS. 6A-6C show an embodiment of a dispenser for the implants described herein.
Figure 6B:
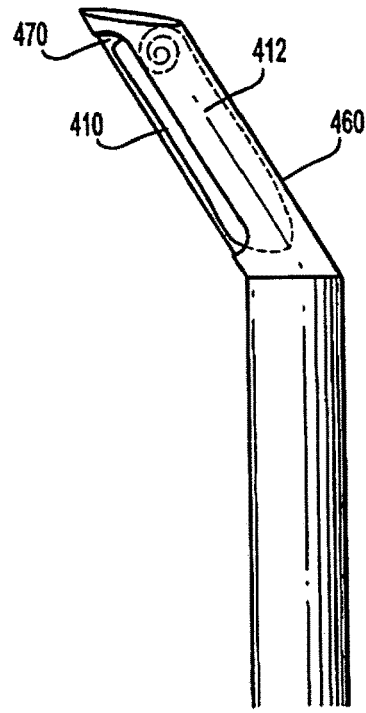
Figure 6C:
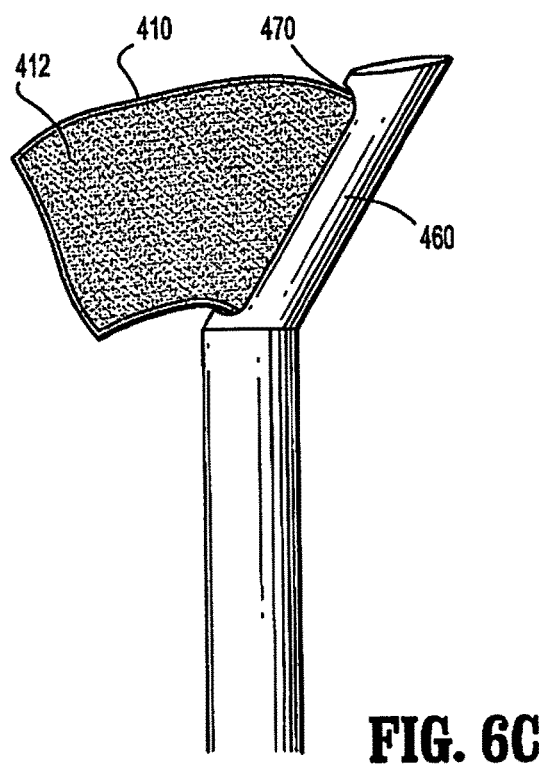

In some embodiments, as shown in FIGS. 6A-6C, dispenser 450 includes dispensing opening 470 and compartment 460 for containing implant 410, rupturable barrier 435 and adhesive 412. Dispenser 450 is shown pivotably connected to surgical introducer 500 which is used to position implant 410 at the site of implantation. It is envisioned that introducer 500 may be used to guide dispenser 450 through any surgical opening or trocar to the site of implantation.

As shown in FIG. 6B, dispenser 450 may pivot or articulate to one side of introducer 500 thereby breaking open rupturable barrier 435 and releasing adhesive 412 on implant 410. As dispenser 450 is articulated in the opposite direction as shown in FIG. 6C, implant 410 may exit or be withdrawn from dispenser 450 via dispensing opening 470 and positioned at the site of implantation. The adhesive will react with the tissue or fluids at the site of implantation securing the implant to the tissue. Once implant 410 is outside dispenser 450, dispenser 450 may return to the straight position as shown FIG. 6A for removal from inside the body.

It is envisioned that dispenser 450 may include additional structures which may be helpful in rupturing rupturable barrier 435 or useful in applying adhesive 412 to implant 410. Some examples are described herein and include, but are not meant to limited to, rollers, brushes, wipers, and the like.

In some embodiments implant 410 may be coated with an adhesive which is designed to react only with the tissue located at the site of implantation and as a result does not react with the implant, the dispenser thereby eliminating the need for a rupturable barrier 435. In some embodiments, implant 410 may include adhesive 412 covered by a release sheet which upon implantation may be removed or dissolved to expose the adhesive on the implant.

The self-adherent implants described herein may additionally include a bioactive agent. The bioactive agent may be combined with the material used to form the implant and/or the adhesive. In addition, the bioactive agent may be applied to a portion of the implant and/or adhesive. The term "bioactive agent", as used herein, is used in its broadest sense and includes any substance or mixture of substances that have clinical use. Consequently, bioactive agents may or may not have pharmacological activity per se, e.g., a dye, or fragrance. Alternatively a bioactive agent could be any agent which provides a therapeutic or prophylactic effect, a compound that affects or participates in tissue growth, cell growth, cell differentiation, an anti-adhesive compound, a compound that may be able to invoke a biological action such as an immune response, or could play any other role in one or more biological processes. It is envisioned that the bioactive agent may be applied to the implant in any suitable form of matter, e.g., films, powders, liquids, gels and the like.

Examples of classes of bioactive agents which may be utilized in accordance with the present disclosure include anti-adhesives, antimicrobials, analgesics, antipyretics, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, and enzymes. It is also intended that combinations of bioactive agents may be used.

Anti-adhesive agents can be used to prevent adhesions from forming between the implants and the surrounding tissues opposite the target tissue. In addition, anti-adhesive agents may be used to prevent adhesions from forming between the implants and the packaging material. Some examples of these agents include, but are not limited to poly(vinyl pyrrolidone), carboxymethyl cellulose, hyaluronic acid, polyethylene oxide, poly vinyl alcohols and combinations thereof.

Suitable antimicrobial agents which may be included as a bioactive agent in the present disclosure include triclosan, also known as 2,4,4'-trichloro-2'-hydroxydiphenyl ether, chlorhexidine and its salts, including chlorhexidine acetate, chlorhexidine gluconate, chlorhexidine hydrochloride, and chlorhexidine sulfate, silver and its salts, including silver acetate, silver benzoate, silver carbonate, silver citrate, silver iodate, silver iodide, silver lactate, silver laurate, silver nitrate, silver oxide, silver palmitate, silver protein, and silver sulfadiazine, polymyxin, tetracycline, aminoglycosides, such as tobramycin and gentamicin, rifampicin, bacitracin, neomycin, chloramphenicol, miconazole, quinolones such as oxolinic acid, norfloxacin, nalidixic acid, pefloxacin, enoxacin and ciprofloxacin, penicillins such as oxacillin and pipracil, nonoxynol 9, fusidic acid, cephalosporins, and combinations thereof. In addition, antimicrobial proteins and peptides such as bovine lactoferrin and lactoferricin B may be included as a bioactive agent in the present disclosure.

Other bioactive agents which may be included as a bioactive agent in accordance with the present disclosure include: local anesthetics; non-steroidal antifertility agents; parasympathomimetic agents; psychotherapeutic agents; tranquilizers; decongestants; sedative hypnotics; steroids; sulfonamides; sympathomimetic agents; vaccines; vitamins; antimalarials; anti-migraine agents; anti-parkinson agents such as L-dopa; anti-spasmodics; anticholinergic agents (e.g. oxybutynin); antitussives; bronchodilators; cardiovascular agents such as coronary vasodilators and nitroglycerin; alkaloids; analgesics; narcotics such as codeine, dihydrocodeinone, meperidine, morphine and the like; non-narcotics such as salicylates, aspirin, acetaminophen, d-propoxyphene and the like; opioid receptor antagonists, such as naltrexone and naloxone; anti-cancer agents; anti-convulsants; anti-emetics; antihistamines; anti-inflammatory agents such as hormonal agents, hydrocortisone, prednisolone, prednisone, non-hormonal agents, allopurinol, indomethacin, phenylbutazone and the like; prostaglandins and cytotoxic drugs; estrogens; antibacterials; antibiotics; anti-fungals; anti-virals; anticoagulants; anticonvulsants; antidepressants; antihistamines; and immunological agents.

Other examples of suitable bioactive agents include viruses and cells, peptides, polypeptides and proteins, analogs, muteins, and active fragments thereof, such as immunoglobulins, antibodies, cytokines (e.g. lymphokines, monokines, chemokines), blood clotting factors, hemopoietic factors, interleukins (IL-2, IL-3, IL-4, IL-6), interferons (β-IFN, (α-IFN and γ-IFN), erythropoietin, nucleases, tumor necrosis factor, colony stimulating factors (e.g., GCSF, GM-CSF, MCSF), insulin, anti-tumor agents and tumor suppressors, blood proteins, gonadotropins (e.g., FSH, LH, CG, etc.), hormones and hormone analogs (e.g., growth hormone), vaccines (e.g., tumoral, bacterial and viral antigens); somatostatin; antigens; blood coagulation factors; growth factors (e.g., nerve growth factor, insulin-like growth factor); protein inhibitors, protein antagonists, and protein agonists; nucleic acids, such as antisense molecules, DNA and RNA; oligonucleotides; polynucleotides; and ribozymes.

Figure 5:
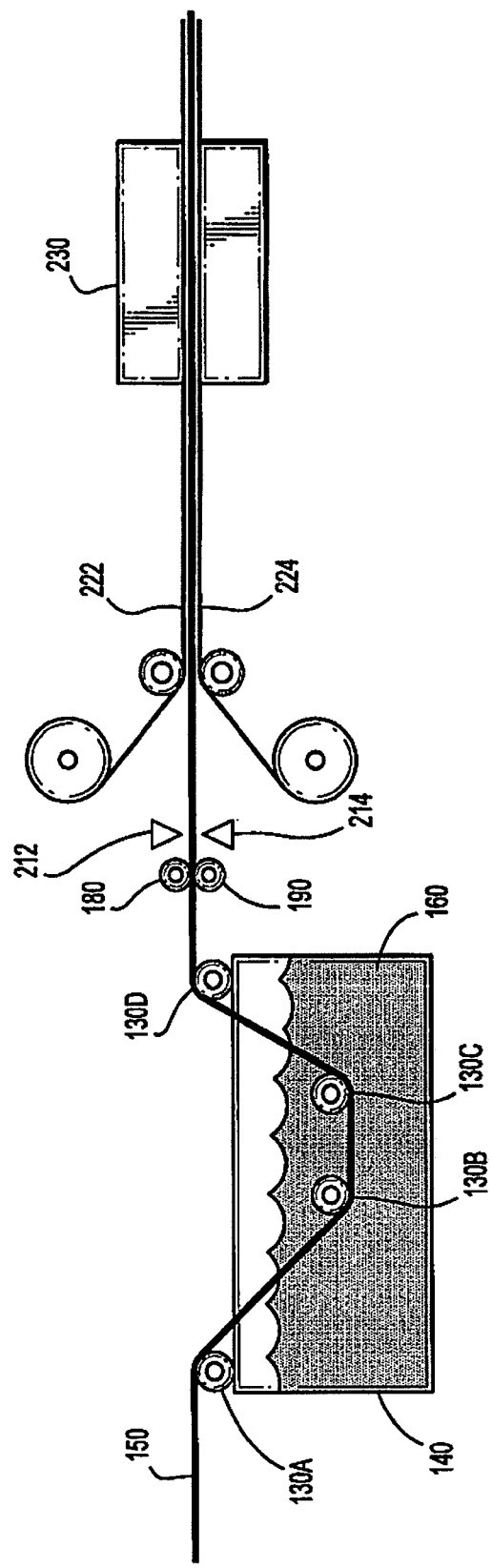
FIG. 5 shows an illustrative embodiment of an apparatus suitable for performing a method of manufacturing an implant in accordance with the present disclosure.

Now turning to FIG. 5, a particularly useful method of preparing self-adherent implants as described herein is shown. Implant 150 is shown being moved horizontally around a series of rollers 130A-D. Implant 150, e.g., a polypropylene surgical mesh, is moved through bath 140 which contains an adhesive solution 160 to be applied to at least a portion of implant 150. Although specifically shown as being dipped in bath 140, adhesive solution 160 can be applied to medical implant 150 in any suitable manner for coating the implant. After exiting bath 140, implant 150 proceeds between a set of pinch rollers 180, 190 which may remove excess adhesive solution 160 and continues through a pair of cutting edges 212, 214. The cutting edges 212, 214 may be forced together to separate implant 150 into predetermined lengths and widths. Once the implant 150 is cut into size, a top layer 224 and a bottom layer 222 of packaging material may be used to "sandwich" the cut implant 150. Medical implant 150, sandwiched between top layer 224 and bottom layer 222, proceeds to enter a sealing device 230 wherein top layer 224 and bottom layer 222 are cut and sealed along the outer perimeter around implant 150. Although specifically shown as being cut by cutting edges 212, 214 prior to being packaged and sealed, implant 150 may be cut, packaged and sealed in any order suitable to producing a sterilized medical implant as described herein.

Since the self-adherent implant is intended and designed to be inserted into the human body, the implant must be sterilized prior to use. The sterilization of the implant, the package which contains the implant and the dispenser which dispenses the packaged implant may be sterilized at anytime, including before and after packaging of the implant. The sterilization process can be performed using various methods known to one skilled in the art, including, gamma radiation and gaseous sterilization with steam or ethylene oxide.

It will be understood that various modifications may be made to the embodiments disclosed herein. For example, it is contemplated that both sides of the implant can be coated with adhesive and that both layers of the package may serve as or include a release sheet. As another example, the structure for rupturing the rupturable barrier may be spring loaded, rather than a simple pair of rollers. As yet another example, the dual compartment package may include in one compartment an implant coated with an inactivated adhesive and an activation solution in the second compartment, rather than an uncoated implant and an adhesive as described above. The activating solution may be water or a composition containing initiators, crosslinkers, diluents and the like. Therefore, the above description should not be construed as limiting, but merely as exemplifications of preferred embodiments. Those skilled in art will envision other modifications within the scope and spirit of the claims appended hereto.

What is claimed is:

1. A dispenser for activating a packaged implant, said dispenser comprising:
   a packaged implant including a medical adhesive and a surgical mesh contained within a peelable package having a top layer and a bottom layer, the top layer and bottom layer defining a first cavity containing the medical adhesive, a second cavity containing the surgical mesh, and a rupturable barrier positioned between the first and second cavity,
   a compartment containing the packaged implant, the compartment including a dispensing opening and a structure for rupturing the rupturable barrier of the packaged implant.

2. The dispenser of claim 1 wherein the medical adhesive is selected from the group consisting of polyurethanes, isocyanates and combinations thereof.

3. The dispenser of claim 1 wherein the rupturable barrier is formed by a portion of a top layer and a bottom layer of the package.

4. The dispenser of claim 1 wherein the structure for rupturing said rupturable barrier comprises a contoured ridge which reduces the size of the opening and includes a smooth surface to rupture the rupturable barrier without tearing open the package.

5. The dispenser of claim 1 further comprising a second structure for applying the medical adhesive to at least a portion of the mesh.

6. The dispenser of claim 5 wherein the second structure for applying the medical adhesive is selected from the group consisting of wipers, rollers, brushes and combinations thereof.

7. The dispenser of claim 6 wherein the second structure for applying the medical adhesive is a roller.

8. The dispenser of claim 1 wherein the dispensing opening is configured to allow for the passage of the packaged implant out of the compartment after the rupturable barrier has been ruptured and at least some of the medical adhesive in the first cavity moves into the second cavity and in contact with the surgical mesh.

9. The dispenser of claim 1 wherein the top and bottom layers define a sealed perimeter of the peelable package.

10. The dispenser of claim 9 wherein the first and second cavities are defined within the sealed perimeter of the peelable package.

* * * * *